US012059282B2

(12) United States Patent
He et al.

(10) Patent No.: US 12,059,282 B2
(45) Date of Patent: Aug. 13, 2024

(54) MEDICAL IMAGING SYSTEM WITH CONTOURED DETECTOR

(71) Applicant: HOLOGIC, INC., Marlborough, MA (US)

(72) Inventors: Shusheng He, Marlborough, MA (US); Brad Polischuk, Marlborough, MA (US); Tuan Huynh, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 592 days.

(21) Appl. No.: 17/276,764

(22) PCT Filed: Sep. 16, 2019

(86) PCT No.: PCT/US2019/051353
§ 371 (c)(1),
(2) Date: Mar. 16, 2021

(87) PCT Pub. No.: WO2020/060947
PCT Pub. Date: Mar. 26, 2020

(65) Prior Publication Data
US 2022/0047232 A1 Feb. 17, 2022

Related U.S. Application Data

(60) Provisional application No. 62/732,308, filed on Sep. 17, 2018.

(51) Int. Cl.
*A61B 6/50* (2024.01)
*A61B 6/04* (2006.01)
(Continued)

(52) U.S. Cl.
CPC ............ *A61B 6/502* (2013.01); *A61B 6/0414* (2013.01); *A61B 6/4291* (2013.01); *A61B 6/025* (2013.01); *A61B 6/4208* (2013.01)

(58) Field of Classification Search
CPC .............................. A61B 6/4291; A61B 6/502
See application file for complete search history.

(56) References Cited

U.S. PATENT DOCUMENTS 4,901,335 A * 2/1990 Ferlic .................. A61B 6/4291
378/155
4,905,269 A * 2/1990 Mosby .................. A61B 6/502
378/182
(Continued)

OTHER PUBLICATIONS

PCT International Preliminray Report on Patentability in International Application PCT/US2019/051353, mailed Mar. 25, 2021, 11 pages.
(Continued)

*Primary Examiner* — Chih-Cheng Kao
(74) *Attorney, Agent, or Firm* — Merchant & Gould P.C.

(57) ABSTRACT

A medical imaging system that includes a contoured radiation detector configured to receive radiation emitted from a radiation source after the radiation has passed through at least a portion of a patient. The contoured radiation detector includes a gate-wall end and lateral sides, including a right-hand side and a left-hand side. The contoured radiation detector may also includes a superior surface connected to the gate-wall end, right-hand side, and the left-hand side. The contoured radiation detector further includes a chest-wall surface, the chest-wall surface connected to the superior surface, the right-hand side, and the left-hand side, whereby the curvature is contoured to a chest wall of the patient. The system may also include an anti-scatter grid having a chest-wall surface with a similar curvature as the chest-wall surface of the contoured radiation detector.

19 Claims, 11 Drawing Sheets

(51) Int. Cl.
*A61B 6/42* (2024.01)
*A61B 6/02* (2006.01)

(56) References Cited

U.S. PATENT DOCUMENTS

| | | |
|---|---|---|
| 4,943,986 A | 7/1990 | Barbarisi |
| 4,943,991 A * | 7/1990 | Mosby ................ A61B 8/4281 |
| | | 378/185 |
| 7,869,563 B2 | 1/2011 | Defreitas et al. |
| 9,226,718 B1 | 1/2016 | Baxley |
| 9,901,315 B2 | 2/2018 | Farbizio et al. |
| 2002/0090055 A1* | 7/2002 | Zur ...................... A61B 6/4291 |
| | | 378/154 |
| 2004/0028176 A1 | 2/2004 | Kamenetsky et al. |
| 2007/0195937 A1 | 8/2007 | Haupl |
| 2008/0080673 A1 | 4/2008 | Yamakita |
| 2011/0033029 A1 | 2/2011 | Klausz |
| 2016/0022230 A1* | 1/2016 | Farbizio ................ A61B 6/025 |
| | | 378/22 |

OTHER PUBLICATIONS

International Search Report and Written Opinion of the International Searching Authority for International Patent Application No. PCT/US2019/051353 mailed Feb. 4, 2020, 18 pages.

\* cited by examiner

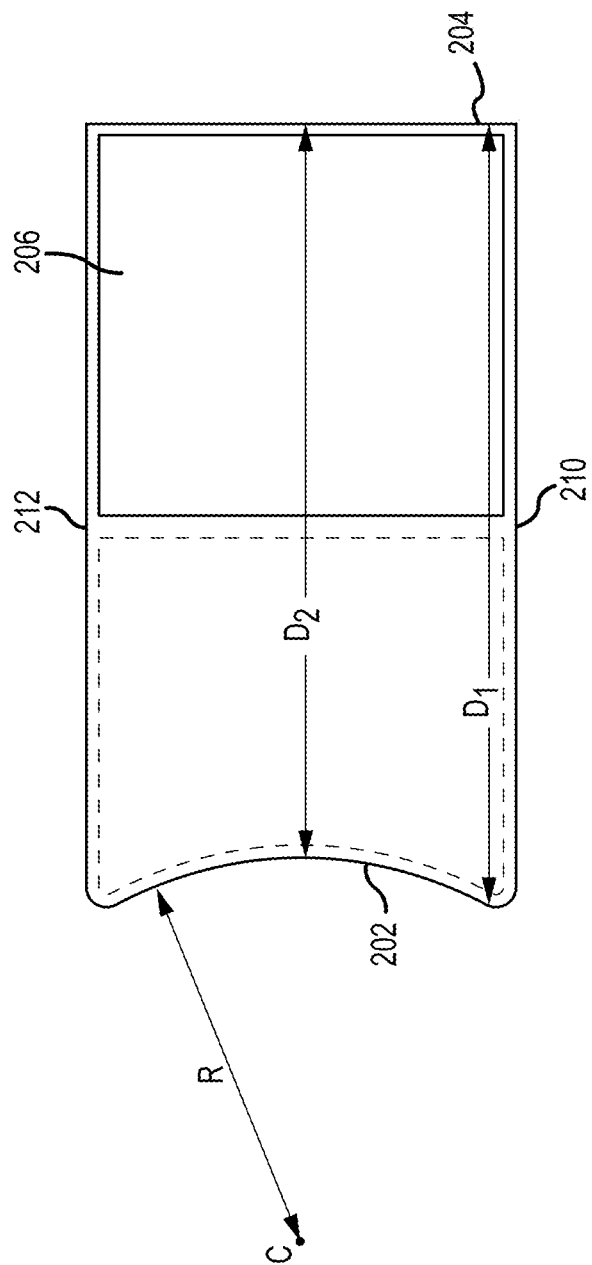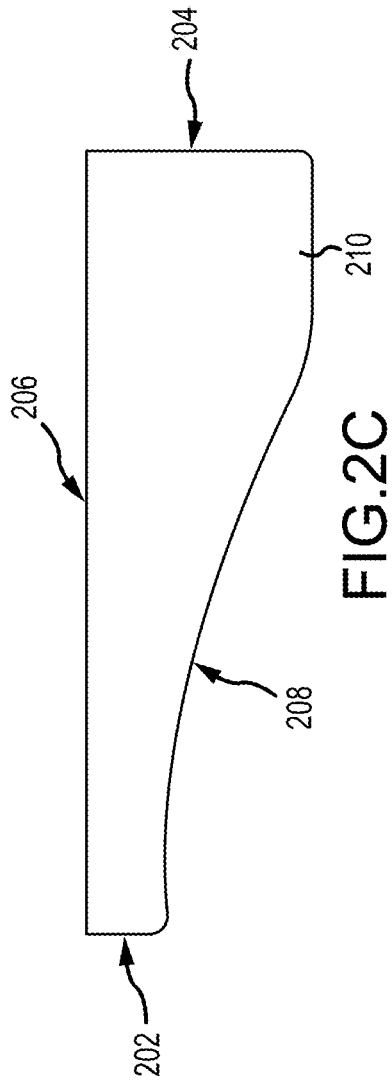

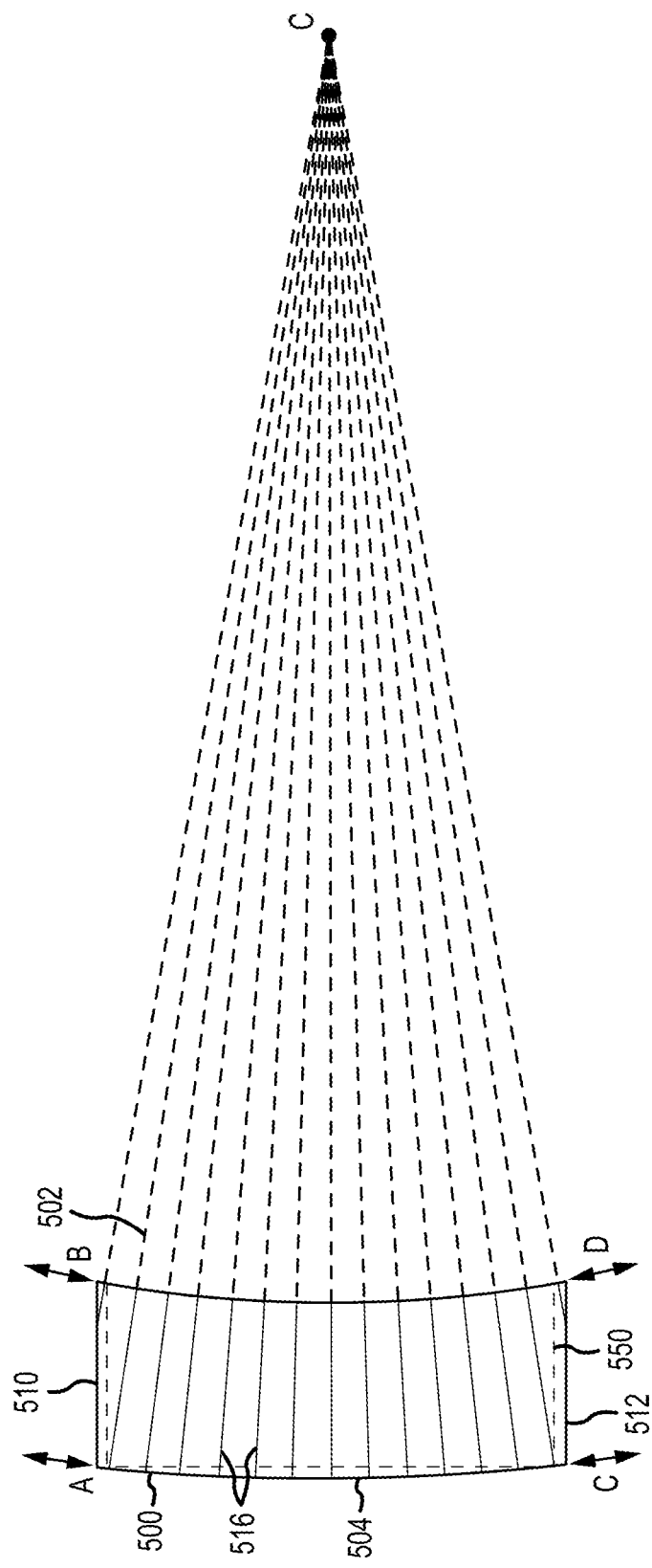

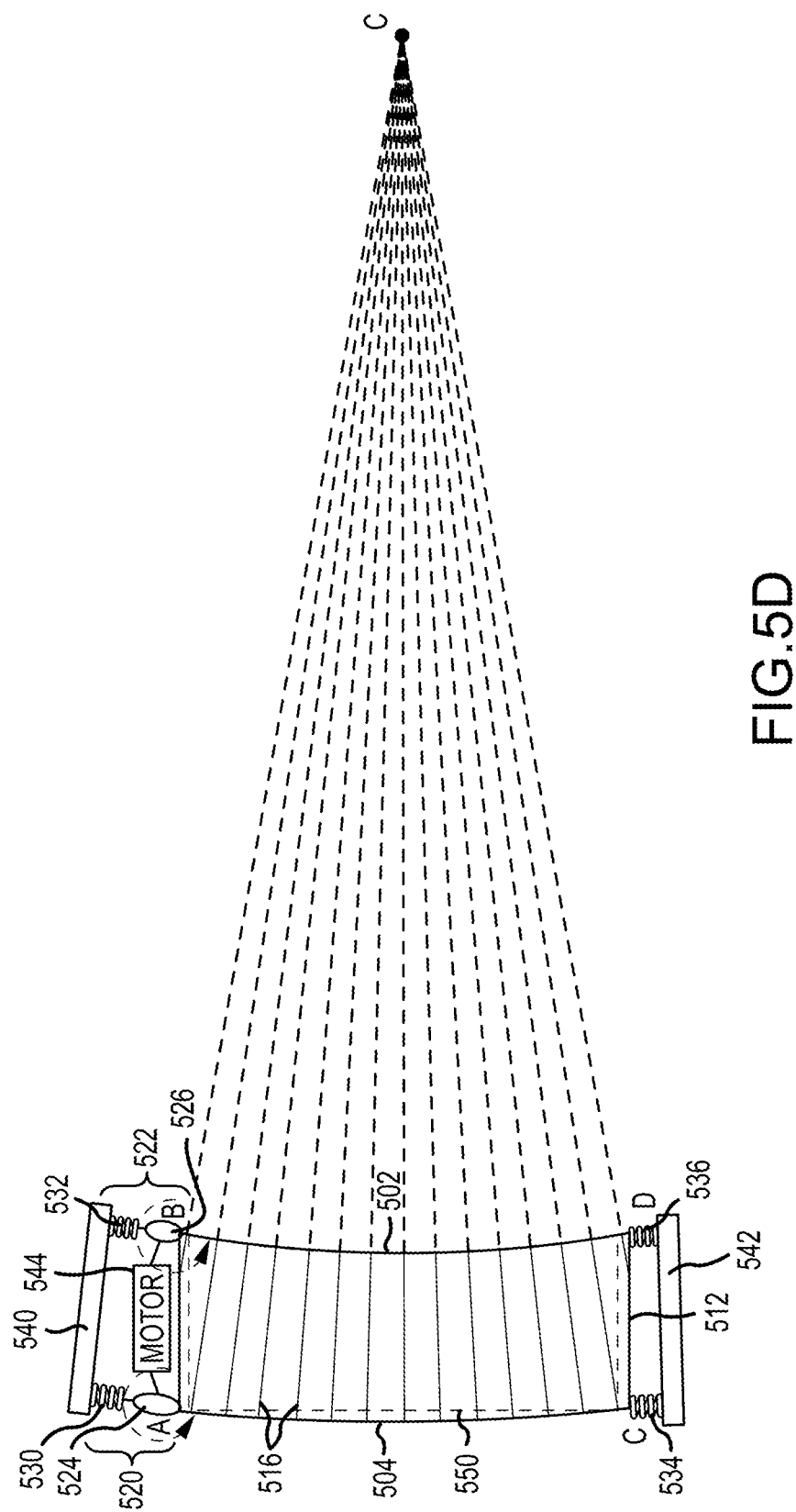

MEDICAL IMAGING SYSTEM WITH CONTOURED DETECTOR

CROSS-REFERENCE TO RELATED APPLICATIONS

This application is a National Stage Application of PCT/US2019/051353, filed Sep. 16, 2019, which claims priority to and the benefit of U.S. Provisional Patent Application No. 62/732,308, filed Sep. 17, 2018, the disclosures of which are hereby incorporated by reference herein in their entireties. To the extent appropriate, a claim of priority is made to each of the above disclosed applications.

BACKGROUND

Medical imaging has become a widely used tool for identifying and diagnosing abnormalities, such as cancers or other conditions, within the human body. Medical imaging modalities such as mammography and tomosynthesis are particularly useful tools for imaging breasts to screen for, or diagnose, cancer or other lesions with the breasts. Tomosynthesis systems are three-dimensional (3D) mammography systems that allow high resolution breast imaging based on limited angle tomography. In contrast to typical two-dimensional (2D) mammography systems, a tomosynthesis system acquires a series of x-ray projection images, each projection image obtained at a different angular displacement as the x-ray source moves along a path, such as a circular arc, over the breast. In contrast to conventional computed tomography (CT), tomosynthesis is typically based on projection images obtained at limited angular displacements of the x-ray source around the breast. Tomosynthesis reduces or eliminates the problems caused by tissue overlap and structure noise present in 2D mammography imaging. Even with such improvements in image quality and results in tomosynthesis, mammography, and CT, it is still useful to be able to image the whole breast and the surrounding tissues. Due to the physical limitations of some medical imaging systems (e.g., size constraints, need to immobilize or compress the soft tissue), however, tissues surrounding the breast, and sometimes portions of the breasts themselves, are not able to be imaged.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for medical imaging with a contoured detector. In an aspect, the technology relates to a medical imaging system that includes a radiation source configured to emit radiation and a contoured radiation detector configured to receive radiation emitted from the radiation source after the radiation has passed through at least a portion of a patient. The contoured radiation detector includes: a gate-wall end; lateral sides, including a right-hand side and a left-hand side; a superior surface connected to the gate-wall end, right-hand side, and the left-hand side; and a chest-wall surface, the chest-wall surface connected to the superior surface, the right-hand side, and the left-hand side, whereby the curvature is contoured to a chest wall of the patient. In an example, the chest-wall surface has a radius of curvature between about 300 and about 600 mm. In another example, the chest-wall surface is substantially orthogonal to the superior surface. In yet another example, the medical imaging system is a tomosynthesis system. In still another example, a center of curvature of the chest-wall surface is outside of the contoured radiation detector. In still yet another example, a distance from a midpoint of the chest-wall surface to the midpoint of the gate-wall end is less than a distance from an end of the chest-wall surface proximate a lateral side to an end of the gate-wall end proximate the lateral side.

In another example, a height of the chest-wall surface is between about 2 cm and about 15 cm. In yet another example, the contoured radiation detector is disposed below a breast support platform of the imaging system. In still another example, the breast platform includes a chest-wall surface that is contoured to substantially match the radius of curvature of the chest-wall surface of the contoured radiation detector. In still yet another example, the medical imaging system further includes an anti-scatter grid above the superior surface, wherein the anti-scatter grid includes: a grid gate-wall end; grid lateral sides, including a grid right-hand side and a grid left-hand side; and a grid chest-wall surface, wherein the grid chest-wall surface has a curvature substantially matching the radius of curvature of the chest-wall surface of the contoured radiation detector.

In another example, the anti-scatter grid is configured to rotationally move around the radius of curvature. In yet another example, the medical imaging system includes a plurality of actuating devices attached to the anti-scatter grid to control movement of the anti-scatter grid. In still another example, one or more of the plurality of actuating devices comprises a motor and an elliptical element, wherein the elliptical element is in contact with one of the grid lateral sides, wherein the motor is configured to rotate the elliptical element such that the anti-scatter grid moves in response to rotation of the elliptical element. In still yet another example, a first actuating device and a second actuating device are in contact with one of the grid lateral sides.

In another example, the first actuating device includes a first elliptical element, wherein the first elliptical element is in contact with one of the grid lateral sides, and the second actuating device includes a second elliptical element, wherein the second elliptical element is in contact with the one of the grid lateral sides. In yet another example, the first elliptical element has a major axis and the second elliptical element has a major axis, wherein the major axis of the first elliptical element is greater than the major axis of the second elliptical element. In still another example, at least one of the first actuating device and the second actuating device includes a motor configured to rotate at least one of the first actuating device and the second actuating device. In still yet another example, at least one spring is attached to a grid lateral side opposite the grid lateral side in contact with the first actuating device and the second actuating device. In another example the medical imaging system further includes a first spring, a second spring, a third spring, and a fourth spring, and wherein: the first elliptical element is in contact with the right-hand side and a first spring; the second elliptical element is in contact with the right-hand side and a second spring; and the left-hand side is in contact with the third spring and the fourth spring.

In another aspect, the technology relates to a medical imaging apparatus that includes a contoured radiation detector configured to detect radiation emitted from a radiation source, wherein the contoured radiation detector includes a contoured chest-wall surface, whereby the curvature is contoured to the chest wall of a patient. In an example, the medical imaging apparatus includes an anti-scatter grid located between the contoured radiation detector and the radiation source, wherein the anti-scatter grid includes a grid chest-wall surface having a curvature that substantially matches the curvature of the curved chest wall surface of the contoured radiation detector. In another example, the anti-scatter grid includes a gate-wall end having a center of curvature that is the same as a center of curvature of the grid chest-wall surface. In yet another example, the anti-scatter grid has a chest-to-gate pitch ratio between about 1.3:1 to 2.0:1. In still another example, the medical imaging apparatus further includes a control system for controlling movement of the anti-scatter grid, the control system comprising a first elliptical element in contact with a lateral side of the anti-scatter grid and a second elliptical element in contact with the lateral side of the anti-scatter grid.

In another example, the ratio of a length of a major axis of the first elliptical element to a length of a major axis of the second elliptical element is about RG/RC, where RG is a radius of curvature of the grid gate-wall end, and RC is a radius of curvature of the grid chest-wall surface. In yet another example, the chest-wall surface of the contoured radiation detector has a radius of curvature between about 50 mm to about 900 mm.

In another aspect, the technology relates to a method of medical imaging. The method includes emitting radiation from a radiation source; and while emitting radiation from a radiation source, rotationally moving an anti-scatter grid positioned between the radiation source and a radiation detector, wherein a chest-wall surface of the anti-scatter grid is curved and has a radius of curvature. Rotationally moving the anti-scatter grid includes rotating a first elliptical element at a first speed, wherein the first elliptical element is in contact with the anti-scatter grid; and rotating a second elliptical element at a second speed, wherein the second elliptical element is in contact with the anti-scatter grid. In an example, the first speed and the second speed are the same. In another example, the first elliptical element has a major axis and the second elliptical element has a major axis and the major axis of the first elliptical element is greater than the major axis of the second elliptical element. In yet another example, rotationally moving the anti-scatter grid moves the anti-scatter grid around a center of curvature of the chest-wall surface of the anti-scatter grid.

In another aspect, the technology relates to a medical imaging system that includes an x-ray source; and a contoured radiation detector having a flat-panel detector facing the x-ray source and a chest-wall surface having a curvature. In an example, the radiation detector further comprises a gate-wall end disposed opposite the chest-wall surface. In another example, the radiation detector further comprises a superior surface connecting the gate-wall end and the chest-wall surface, wherein the flat-panel radiation detector is disposed in the superior surface. In yet another example, the medical imaging system further includes lateral sides, including a right-hand side and a left-hand side, wherein the lateral sides are connected to the chest-wall surface and the superior surface. In still another example, a distance from a midpoint of the chest-wall surface to the midpoint of the gate-wall end is less than a distance from an end of the chest-wall surface proximate a lateral side to an end of the gate-wall end proximate the lateral side. In still yet another example, a center of curvature of the chest-wall surface is outside of the contoured radiation detector.

In another example, the chest-wall surface has a radius of curvature between about 300 and about 600 mm. In yet another example, the chest-wall surface is substantially orthogonal to the superior surface. In still another example, the medical imaging system further comprises a contoured compression plate a chest-wall surface having a curvature. In still yet another example, the curvature of the chest-wall surface of the contoured compression plate is substantially the same as the curvature of the chest-wall surface of the contoured radiation detector.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIG. 2B depicts a top view of the example contoured radiation detector.

FIG. 2C depicts a side view of the example contoured radiation detector.

FIG. 5C depicts a top view of another example of an anti-scatter grid.

FIG. 5D depicts an example of a control system for an anti-scatter grid.

DETAILED DESCRIPTION

Figure 1:
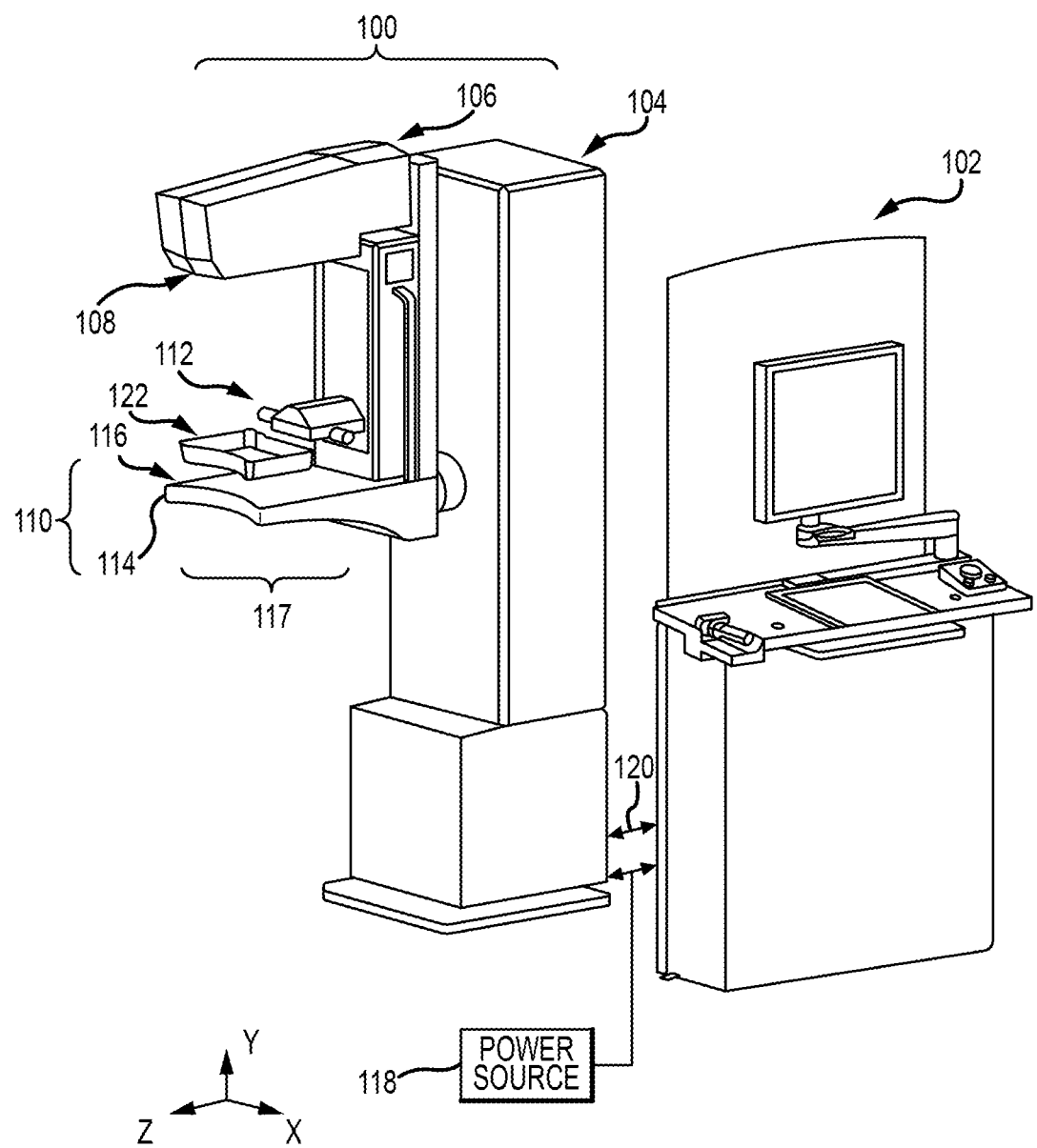
FIG. 1 depicts an example of a medical imaging system, such as a multi-mode mammography/tomosynthesis system.

As discussed above, in most types of medical imaging of a breast, it is preferable to be able to image the entire breast and the surrounding tissue. The physical structure of some current tomosynthesis and mammography systems, however, limit the amount of the breast and surrounding tissue that can be imaged. For example, in a mammography or tomosynthesis system, the surface of the breast platform that contacts the chest wall of the patient is straight. Because the surface is straight, the surface does not match the contour of the human body, thus causing portions of the chest wall of the patient to necessarily be further from, and possibly out of range of, the imaging area. As a result, tissue surrounding the breast may not be imaged during a mammography or tomosynthesis procedure. The use of straight detector or platform may also result in additional discomfort for the patient. For instance, in some cases, a technician may attempt to press the patient closer into the platform and hold the patient in such a position in order to try to image tissue at or near the chest wall or axilla.

To alleviate at those issues, the present technology introduces a contoured radiation detector and a contoured breast platform that is more closely contoured to the shape of the chest wall of the human body. More specifically, the surface of the breast platform and the radiation detector facing the chest wall of the patient is contoured in a manner that allows more of the tissue surrounding the breast to be imaged by having more of the tissue within the imaging area. With more tissue in the imaging area, the possibility of missing abnormalities within that tissue is reduced. The additional tissue may also be imaged without having to press the patient into the platform—resulting in additional comfort for the patient during the imaging process.

The introduction of a contoured detector, however, also introduces additional challenges in obtaining diagnostic quality images and detecting x-rays. As one challenge, the anti-scatter grid and its movement control systems must also be altered. Anti-scatter grids are used to prevent blurring from scattered x-rays, which degrade the quality of x-ray images. Anti-scatter grids are typically used in conventional x-ray imaging systems to reduce x-ray scatter by selectively blocking scattered x-rays, such as Compton scattered x-rays, while allowing primary x-rays to reach the x-ray detector. Thus, an anti-scatter grid enhances image quality and tissue contrast by reducing the number of detected x-rays that have been scattered by tissue. The anti-scatter grid is also configured to move or vibrate, during x-ray exposure, relative to the x-ray detector to blur out or prevent Moire patterns. Additional details regarding the anti-scatter grids for use in tomosynthesis systems can be found in U.S. Pat. No. 9,901,315, which is incorporated by reference herein in its entirety.

Former anti-scatter grids were rectangular and had straight edges, similar to the former x-ray detectors. Such a rectangular grid is unsuitable for use with a contoured detector. Thus, the present technology incorporates a contoured anti-scatter grid that has a surface facing the chest wall of the patient that is contoured to substantially match the curvature of the x-ray detector. A new system and method for controlling the movement of the x-ray grid is also introduced. Even with an anti-scatter grid having a geometry and curvature that substantially matches the curvature of the x-ray detector, traditional lateral movement of the grid is ineffective because the grid would contact the inside of the chest-wall surface of the breast platform. Accordingly, the present technology introduces a movement system to allow for rotational movement around the center of curvature of the contoured chest-wall surface.

FIG. 1 depicts a non-limiting example of a medical imaging system, such as a multi-mode mammography/tomosynthesis/CT system. The system comprises a gantry 100 and a data acquisition workstation 102. Gantry 100 includes a housing 104 supporting a tube arm assembly 106 rotatably mounted thereon to pivot about a horizontal axis and carrying a radiation source 108 in the form of an x-ray tube assembly. In an example, x-ray tube assembly includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot (2) supports for multiple filters such as molybdenum, rhodium, aluminum, copper, and tin filters, and (3) an adjustable collimation assembly selectively collimating the x-ray beam from the focal spot in a range such as from 7×8 cm to 24×29 when measured at the image plane of an x-ray image receptor included in the system, at a maximum source-image distance such as 75 cm. Also mounted on housing 104, for rotation about the same axis, is a compression arm assembly 110 that comprises a compression plate 122 and a breast platform 114 that houses a curved or contoured radiation or x-ray detector. The breast platform 114 has an upper surface 116 serving as a breast plate and enclosing a detector subsystem 117 comprising a flat panel contoured radiation detector, an anti-scatter grid, and a control system for controlling the movement of the anti-scatter grid.

As can be seen in FIG. 1, the surface of the breast platform 114 that would contact the chest wall of the patient is contoured. The curvature of that surface is contoured to more closely match the curvature of the chest wall of the patient. The contoured radiation detector housed within the breast platform 114 also has a contoured chest-wall surface, as discussed further below with reference to FIGS. 2A-2C. The geometry of the breast platform may be made to substantially match that of the contoured radiation detector. In particular, the contoured chest-wall surface of the breast platform may have a substantially similar radius of curvature or a shared center of curvature as the contoured chest-wall surface of the x-ray detector. In some examples, the chest wall surface of the breast platform may have a radius of curvature smaller than the radius of curvature the chest-wall surface of the contoured radiation detector. In such examples, the center of curvature for the chest-wall surfaces of the breast platform and the x-ray detector may be the same. Full field and/or mid-field imaging may still be accomplished with the contoured detector. In some examples, the surface of the compression plate 122 that would contact the chest wall of the patient is also contoured. The curvature of the compression plate 122 may be the same or substantially similar to the curvature of the breast platform 114 and/or the contoured radiation detector.

Housing 104 may also enclose additional components to facilitate movement of the system, such as a vertical travel assembly for moving tube arm assembly 106 and compression arm assembly 110 up and down to accommodate a particular patient or imaging position, a tube arm assembly rotation mechanism to rotate tube arm assembly 106 for different imaging positions, a detector subsystem rotation mechanism for rotating components of detector subsystem 117 (such as the contoured radiation detector) to accommodate different operation modes, and a couple/uncouple mechanism to selectively couple or uncouple tube arm assembly 106 and compression arm assembly 110 to and from each other, and tube arm assembly 106 and detector subsystem 117 to and from each other. Housing 104 may also enclose suitable motors and electrical and mechanical components and connections to implement the functions discussed here. Workstation 102 comprises components similar to those in the Selenia® Dimensions® or 3Dimensions™ mammography system available from Hologic, Inc. of Marlborough, Massachusetts, including a display screen (typically a flat panel display that may include touch-screen functionality), user interface devices such as a keyboard, possibly a touch-screen, and a mouse or trackball, and various switches and indicator lights and/or displays. Workstation 102 also includes computer facilities similar to those of the Selenia Dimensions system, (but adapted through hardware, firmware and software differences) for controlling gantry 100 and for processing, storing and displaying data received from gantry 100. A power generation facility for x-ray tube assembly 108 may be included in housing 104 or in workstation 102. A power source 118 powers workstation 102. Gantry 100 and workstation 102 exchange data and controls over a schematically illustrated connection 120. Additional details regarding operation of the gantry and workstation are discussed in U.S. Pat. No. 7,869,563, which is incorporated herein by reference in its entirety.

Figure 2A:
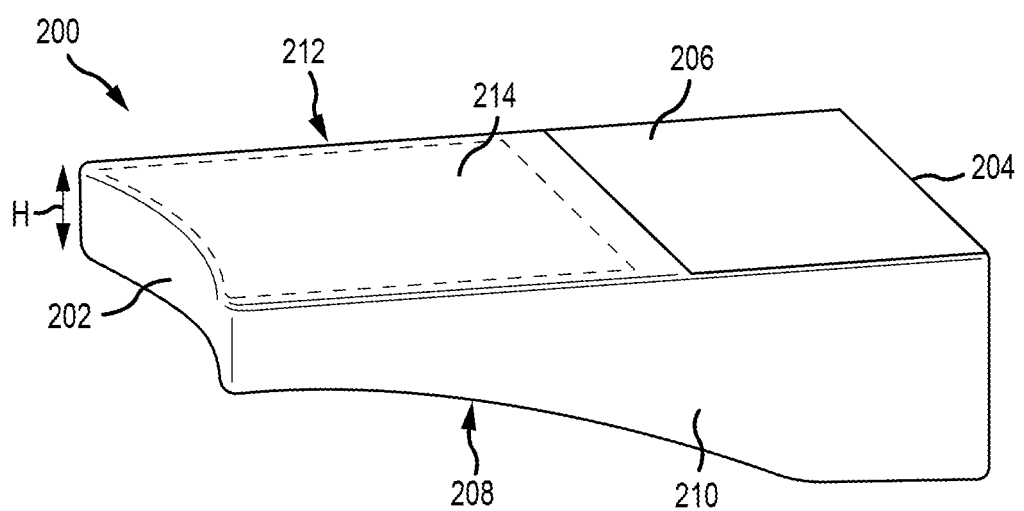
FIG. 2A depicts a perspective view of an example contoured radiation detector.

FIG. 2A depicts a perspective view of an example contoured radiation detector 200. FIG. 2B depicts a top view of the contoured radiation detector 200, and FIG. 2C depicts a side view of the contoured radiation detector 200. FIGS. 2A-2C are discussed concurrently herein. The contoured radiation detector 200 has a chest-wall surface 202 and a gate-wall end 204. The contoured radiation detector 200 also has two lateral sides—a right-hand side 210 and a left-hand side 212. The two lateral sides 210, 212 connect the chest-wall surface 202 and the gate-wall end 204. The example contoured radiation detector 200 also includes a superior surface 206 and an anterior surface 208. The superior surface 206 is connected to the chest-wall surface 202, the gate-wall end 204, the right-hand side 210, and the left-hand side 212. The anterior surface 208 is similarly connected to the chest-wall surface 202, the gate-wall end 204, the right-hand side 210, and the left-hand side 212. The chest-wall surface 202 may be substantially orthogonal to the superior surface 206. The chest-wall surface 202 may also be substantially orthogonal to the right-hand side 210 and/or the left-hand side 212. The superior surface 206 may also be orthogonal to the right-hand side 210 and/or the left-hand side 212. The chest-wall surface 202 has a height (H) that may be constant or variable as the chest-wall surface 202 progresses from the right-hand side 210 to the left-hand side 212. In some examples, the height (H) of the chest-wall surface 202 is between about 2 cm and about 15 cm.

X-ray sensing elements 214 are located on or below the surface of the superior surface 206. The x-ray sensing elements 214 receive x-ray energy after having been emitted from a radiation source and passing through the breast. The x-ray sensing elements 214 convert the received x-ray energy into an electric signal that can be processed and ultimately converted to an image of the breast. The x-ray sensing elements 214 may be part of a flat-panel x-ray sensor as depicted in FIGS. 2A-2C. The superior surface 206 may also be substantially flat to match the upper surface of the x-ray sensing elements 214. The x-ray sensing elements 214 are located near the edge of the chest-wall surface 202 and extend toward the gate-wall end 204. The x-ray sensing elements 214 may be direct conversion technology. For instance, the x-ray sensing elements 214 may include x-ray photoconductors that directly convert photons into an electric charge that can be used to generate the images discussed herein.

The chest-wall surface 202 has a radius of curvature (R), which can be seen most clearly in FIG. 2B. The center of curvature (C) is also illustrated in FIG. 2B, and the center of curvature (C) is located outside the contoured radiation detector 200. The radius of curvature (R) may be between about 50 mm to about 900 mm, depending on the size and configuration of the detector as well as the size of a particular patient or common size of patients most frequently imaged by the medical imaging system. In other examples, the radius of curvature (R) may be between about 100-800 mm, 200-700 mm, 300-600 mm, or 450-550 mm. In other examples, the radius of curvature (R) may be greater than or equal to about 300 mm or less than or equal to about 700 mm. Due to the radius of curvature (R) of the chest-wall surface 202, the distance from the chest-wall surface 202 to the gate-wall end 204 changes from the right-hand side 210 to the left-hand side 212. For example, a distance (D1) from the chest-wall surface 202 to the gate-wall end 204 near either the right-hand side 210 or left-hand side 212 is greater than a distance (D2) from the chest-wall surface 202 to the gate-wall end 204 near the midpoint (MP) of the gate-wall end 204 and the chest-wall end 202. In some examples, where the center of curvature (C) is aligned with the midpoint (MP) of the contoured radiation detector 200, the minimum distance from the chest-wall surface 202 to the gate-wall end 204 occurs at the midpoint (MP). The corners between the chest-wall surface 202 and the lateral sides 210, 212 may also be curved or rounded. The curved or rounded corners may be provided to add additional comfort to the patient when the chest wall of the patient is in contact with the chest-wall surface of the breast platform.

Figure 2D:
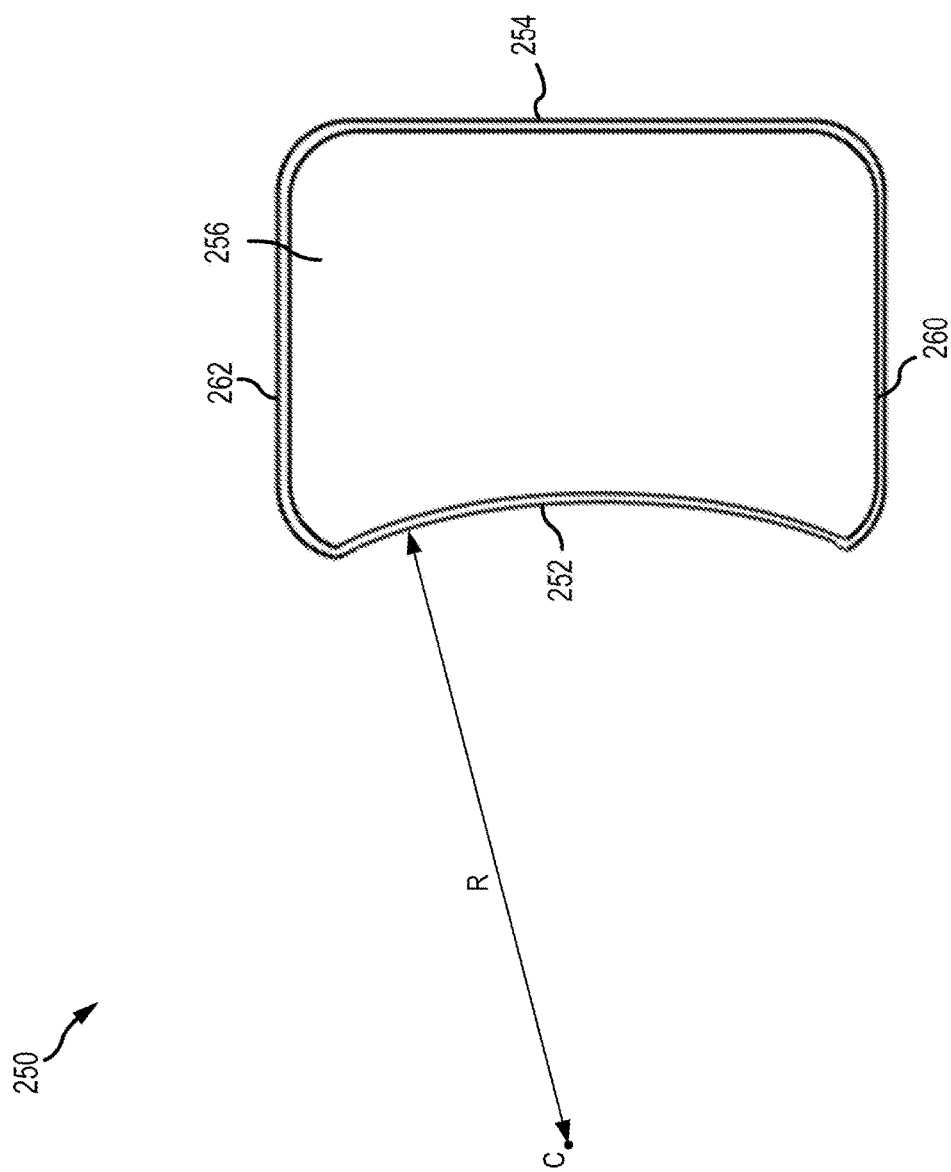
FIG. 2D depicts a top view of a contoured compression plate.

FIG. 2D depicts a top view of a contoured compression plate 250. The contoured compression plate 250 has a chest-wall surface 252 and a gate-wall end 254. The contoured compression plate 250 also has two lateral sides—a right-hand side 260 and a left-hand side 262. The two lateral sides 260, 262 connect the chest-wall surface 252 and the gate-wall end 254. The example contoured compression plate 250 also includes a superior surface 256 and a compression surface (not shown) on the underside of the compression plate. The superior surface 256 is connected to the chest-wall surface 252, the gate-wall end 254, the right-hand side 250, and the left-hand side 252.

The chest-wall surface 252 of the contoured compression plate 250 may be contoured or have substantially the same curvature as the chest-wall surface 202 of the contoured radiation detector 200. For instance, the chest-wall surface 252 of the contoured compression plate 250 has a radius of curvature (R) and a center of curvature (C). The center of curvature (C) is located outside the contoured compression plate 250. The radius of curvature (R) may be between about 50 mm to about 900 mm, depending on the size and configuration of the compression plate 250 as well as the size of a particular patient or common size of patients most frequently imaged by the medical imaging system. In other examples, the radius of curvature (R) may be between about 100-800 mm, 200-700 mm, 300-600 mm, or 450-550 mm. In other examples, the radius of curvature (R) may be greater than or equal to about 300 mm or less than or equal to about 700 mm. In operation, the chest-wall surface 252 of the contoured compression plate 250 may be aligned with the chest-wall surface of contoured radiation detector 200 and/or the chest-wall surface of the breast platform housing the contoured radiation detector 200.

Figure 3:
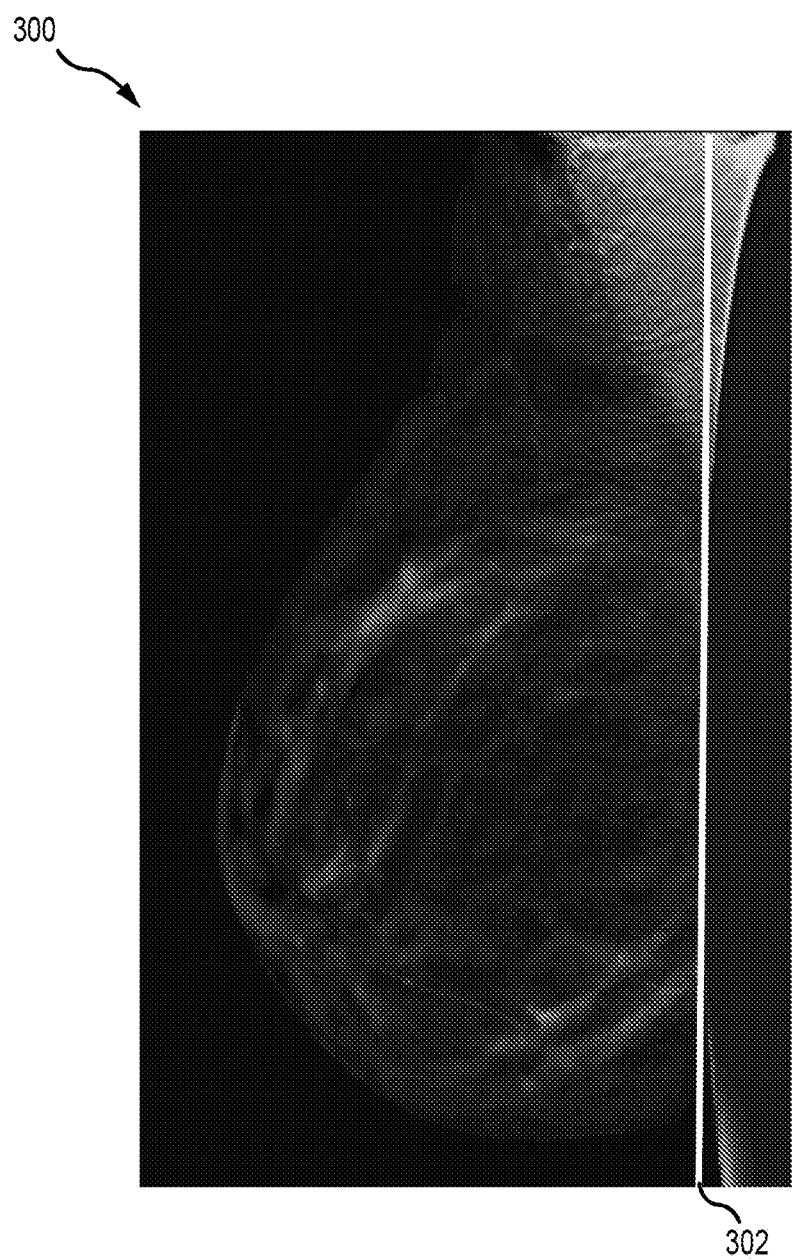
FIG. 3 depicts an example x-ray image of a breast that identifies the additional tissue that can be captured through the use of the contoured radiation detector.

As discussed above, the inclusion of a contoured chest-wall surface allows for additional tissue surrounding the breast to be imaged. Because the chest-wall surface is contoured to more closely match the chest wall of the patient, a larger portion of the detector (and the x-ray sensing elements) patient can be placed in between the radiation source and the contoured radiation detector. FIG. 3 shows an example x-ray image 300 of a breast that identifies the additional tissue that can be imaged through the use of the contoured detector. The image to the left of the vertical line 302 is an image that could have been obtained with a traditional straight-edge detector. With the contoured detector, the additional tissue shown to the right of the vertical line 302 can be imaged. Accordingly, abnormalities such as cancers or lesions that present themselves in that additional tissue can be detected, whereas previous systems may have been unable to do the same without additional imaging procedures and/or painful positioning techniques.

Figure 4:
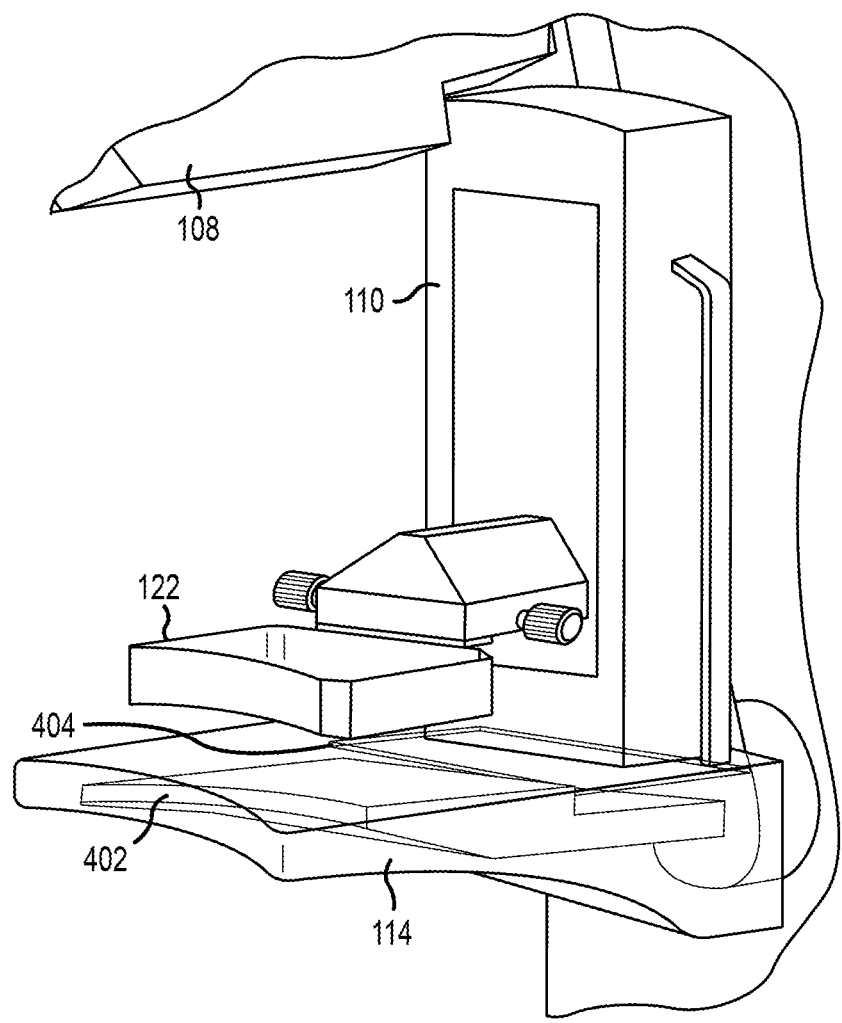
FIG. 4 depicts an enlarged view of a portion of the medical imaging system of FIG. 1.

FIG. 4 depicts an enlarged view of a portion of the medical imaging system of FIG. 1. In particular, FIG. 4 illustrates the components housed within the breast platform 114. For example, housed within the breast platform 114 is the contoured radiation detector 402 and an anti-scatter grid 404. A mechanism for driving and retracting the anti-scatter grid 404 may also be housed or connected to the breast platform 114. In some examples, the anti-scatter grid 404 may be retractable. As discussed above, anti-scatter grids may be used to reduce the image degrading effects of scattered radiation on the image. Stationary anti-scatter grids can cause Moire pattern artifacts that are especially troublesome in a digital x-ray detector, for example due to the interference of the anti-scatter grid pattern with the pixel pattern of the x-ray detector. Thus, the resulting image exhibits Moire patterning or grid line artifacts that degrade image quality. The anti-scatter grids discussed herein, such as anti-scatter grid 404, allow for the reduction or correction of Moire patterns for use in tomosynthesis. In some embodiments, the anti-scatter grid 404 may move relative to the x-ray detector 402, during x-ray exposure, to blur out Moire patterns. Example configurations of anti-scatter grids and movement controls for those anti-scatter grids are discussed further below with reference to FIGS. 5A-5C and FIG. 6.

Figure 5A:
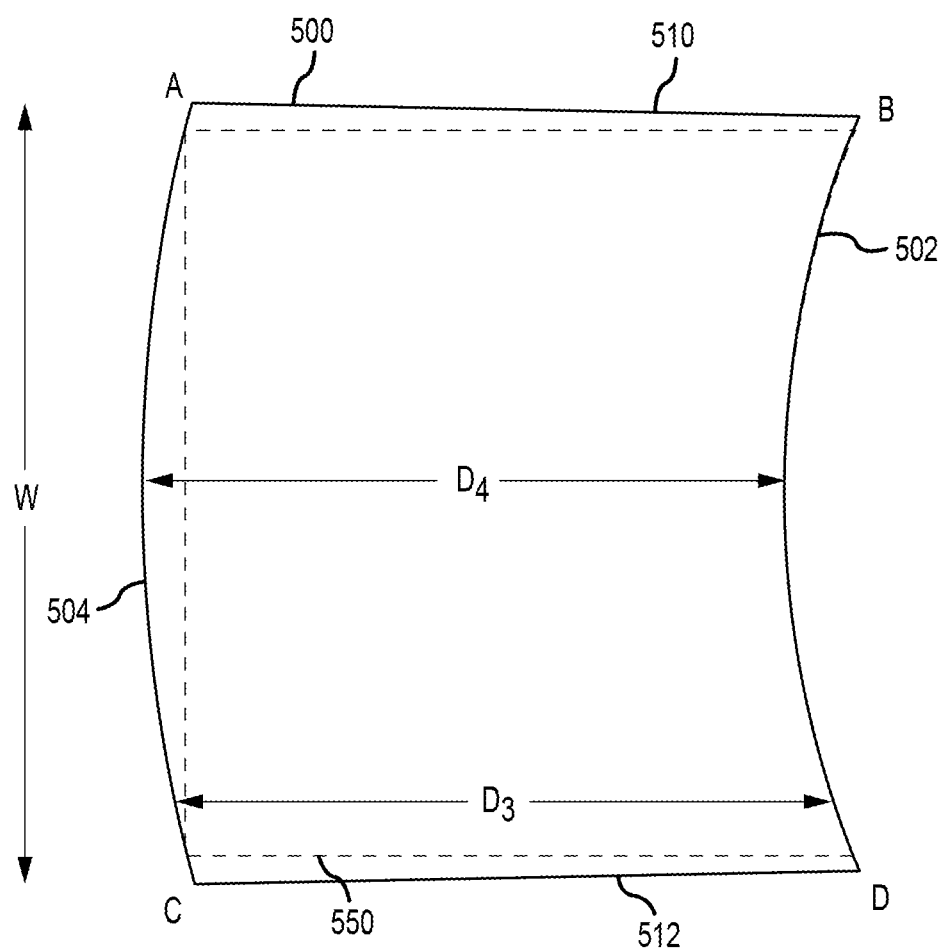
FIG. 5A depicts a top view of an example of an anti-scatter grid.

FIG. 5A depicts a top view of example anti-scatter grid 500. The anti-scatter grid 500 is depicted as being above a contoured radiation detector 550 which, as discussed above, is a common configuration for the anti-scatter grid 500 and the contoured radiation detector 550. The anti-scatter grid 500 shares a similar geometric structure as the contoured radiation detector 550. For example, the anti-scatter grid 500 includes a grid chest-wall surface 502 and a grid gate-wall end 504. The grid chest-wall surface 502 extends between points B and D, and the grid gate-wall end 504 extends between points A and C. The anti-scatter grid 500 also has two grid lateral sides—a grid right-hand side 510 and a grid left-hand side 512. The two grid lateral sides connect the grid chest-wall surface 502 and the grid gate-wall end 504. The grid right-hand side 510 extends between points A and B, and the grid left-hand side extends between points C and D. The example anti-scatter grid 500 also includes a grid superior surface 506 and a grid anterior surface (not shown, the underside of the grid 500). The grid superior surface 506 is connected to the grid chest-wall surface 502, the grid gate-wall end 504, the grid right-hand side 510, and the grid left-hand side 512. The grid anterior surface is similarly connected to the grid chest-wall surface 502, the grid gate-wall end 504, the grid right-hand side 510, and the grid left-hand side 512. The grid anterior surface faces the superior (e.g., top) surface of the contoured radiation detector 550. The grid chest-wall surface 502 may be substantially orthogonal to the grid superior surface 506. The grid chest-wall surface 502 may also be substantially orthogonal to the grid right-hand side 510 and/or the grid left-hand side 512. The grid superior surface 506 may also be orthogonal to the grid right-hand side 510 and/or the grid left-hand side 512.

The grid chest-wall surface 502 has a radius of curvature (R) and a center of curvature (C) similar to the radius of curvature for the contoured radiation detector 550. The radius of curvature (R) and the center of curvature (C) for grid chest-wall surface 502 may have the same dimensions and characteristics as the contoured radiation detector 550, as discussed above. For instance, the radius of curvature (R) may be between about 50 mm to about 900 mm, depending on the size and configuration of the detector as well as the size of a particular patient or common size of patients most frequently imaged by the medical imaging system. In other examples, the radius of curvature (R) may be between about 100-800 mm, 200-700 mm, 300-600 mm, or 450-550 mm. In other examples, the radius of curvature (R) may be greater than or equal to about 300 mm or less than or equal to about 700 mm.

The grid gate-wall end 504 may also be contoured. The grid gate-wall end 504 may have a larger radius of curvature (R) than the grid chest-wall surface 502 but share a common center of curvature (C). In such an example, the distance from the grid chest-wall surface 502 to the grid gate-wall end 504 remains constant from the grid right-hand side 510 to the left-hand side 512. For example, a distance (D3) from the grid chest-wall surface 502 to the grid gate-wall end 504 near either the grid right-hand side 510 or the grid left-hand side 512 may be the same as the distance (D4) from the grid chest-wall surface 502 to the grid gate-wall end 504 near the midpoint of the grid gate-wall end 504. In other examples, the grid gate-wall end 504 may be straight, similar to the gate-wall end of the contoured radiation detector 550. The corners between the grid chest-wall surface 502 and the grid lateral sides 510, 512 may also be curved or rounded.

The anti-scatter grid 500 may be slightly larger than the contoured radiation detector 550 to provide full coverage of the contoured radiation detector 550 even when the anti-scatter grid 500 moves. For instance, the anti-scatter grid 500 may have a larger width (W) than the contoured radiation detector 550. In such examples, the anti-scatter grid 500 may overhang the contoured radiation detector 550 on each lateral side by about 1 mm to 10 mm. In other examples, the anti-scatter grid 500 may overhang the contoured radiation detector 550 on each lateral side by about 10-50 mm. Due to the curvature of the grid gate-wall end 504, a portion of the anti-scatter grid 500 near the grid gate-wall end 504 may also overhang the contoured radiation detector 550. The rear corners of the contoured radiation detector 550 may also lie underneath the anti-scatter grid 500 at a location tangent to the grid gate-wall end 504. For example, as depicted in FIG. 5A, the corner connecting the right-hand side and the gate-wall end of the contoured radiation detector 550 is tangent to the grid gate-wall end 504. Similarly, the corner connecting the left-hand side and the gate-wall end of the contoured radiation detector 550 is tangent to the grid gate-wall end 504.

Figure 5B:
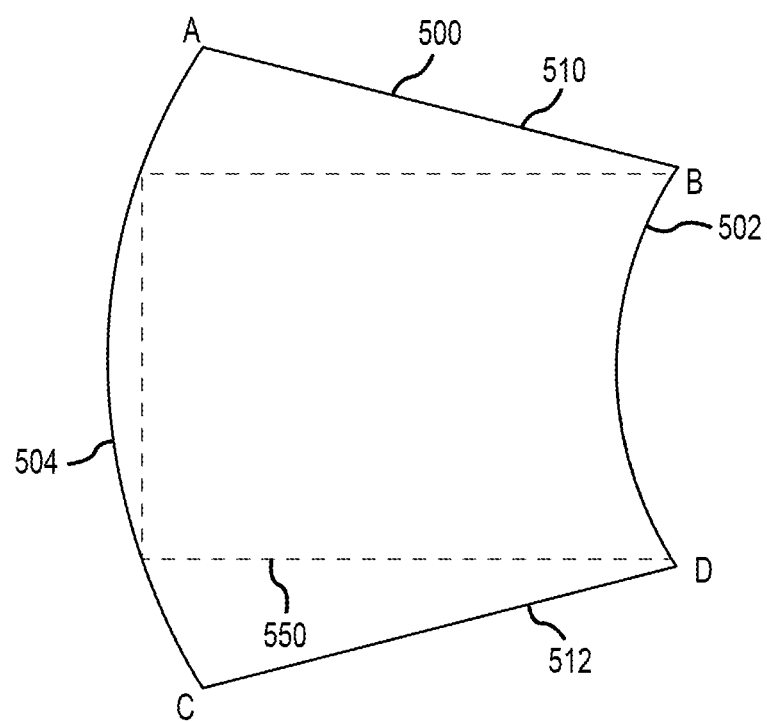
FIG. 5B depicts a top view of another example of an anti-scatter grid.

FIG. 5B depicts the example anti-scatter grid 500 in a different configuration. The anti-scatter grid 500 depicted in FIG. 5B differs from the anti-scatter grid 500 depicted in FIG. 5A in that the anti-scatter grid 500 in FIG. 5B overhangs the edges of the contoured radiation detector 550 more substantially. In such an example, the anti-scatter grid 500 may overhang the anti-scatter grid 500 on each lateral side by about 0.5 cm to 6 cm. In other examples, the anti-scatter grid 500 may overhang the anti-scatter grid 500 on each lateral side by about 1 cm to 3 cm. Due to this increased overhang, the edges of the anti-scatter grid 500 are disposed at a greater angle to each other than the edges of the anti-scatter grid depicted in FIG. 5A.

FIG. 5C depicts the anti-scatter grid 500 in a configuration substantially similar to the configuration depicted in FIG. 5A. The anti-scatter grid 500 depicted in FIG. 5C shows an arrangement of a plurality of septa 516. Each septum 516 is perpendicular to the grid chest-wall surface 502. In other words, each septum 516 is disposed parallel to radius of a circle having the same radius of curvature and center as the grid chest-wall surface 502. In examples where the grid gate-wall end 504 has the same center of curvature as the grid chest-wall surface 502, each of the septa 516 will have substantially the same length. Due to the curvature of the grid chest-wall surface 502 and the grid gate-wall end 504, however, the line pitch of the anti-scatter grid 500 differs from the portion of the anti-scatter grid 500 near the grid chest-wall surface 502 to the grid gate-wall end 504. Near the grid chest-wall surface 502, the pitch may be between about 120-160 μm or about 141 μm. Near the grid gate-wall end 504, the pitch may be about 200-240 μm or 226 μm. The ratio of the pitch near the grid chest-wall surface 502 to the pitch near the grid gate-wall end 504 (referred to herein as the "chest-to-gate pitch ratio") may be between about 1.3:1 to 2.0:1. In some examples the chest-to-gate pitch ratio is about 1.4:1, 1.5:1, 1.6:1, or 1.7:1, or 1.8:1. In some examples, the line density may be about 35-41 lines per centimeter. The pitch and density of the septa 516 have not been drawn to scale.

FIG. 5D depicts a control system for controlling the movement of the anti-scatter grid 500. As discussed above, traditional lateral movement of the grid is unsuitable for the curved anti-scatter grid 500 because the corners of the grid chest-wall surface 502 would contact the breast platform enclosure or the patient, depending on the configuration. As such, a system for providing angular movement to the grid is provided for in the control system depicted in FIG. 5D. By providing angular movement of the anti-scatter grid 500, each of the septa 516 may move with the same angular speed around the center of curvature of the grid chest-wall surface 502.

The control system includes two actuating devices 520, 522 that are in contact with at least one of the grid lateral sides 510, 512. The actuating devices 520, 522 are configured to move the grid gate-wall end 504 a different distance than the grid chest-wall surface 502. By doing so, an angular or rotational motion of the anti-scatter grid 500 around the center of curvature of the grid chest-wall surface 502 can be achieved. In particular, the first actuating device 520 and the second actuating device 522 are configured to move the grid gate-wall end 504 further than the grid chest-wall surface 502 for each movement. The actuating devices 520, 522 are configured to move the grid 500 back and forth in a fairly rapid manner to cause the grid to vibrate in an angular manner around the center of the radius of curvature—thus improving image clarity as discussed above.

In the specific example control system depicted in FIG. 5D, the first actuating device 520 includes a first elliptical element 524 in contact with the grid right-hand side 510 and a first spring 530. The first spring 530 is attached to a support structure 540. The support structure 540 may be a portion of the breast platform housing or may be a separate structure that allows for retraction of the anti-scatter grid 500. The first elliptical element 524 has a major axis and a minor axis. The first elliptical element 524 is attached to a motor 544 that causes the first elliptical element to rotate or spin.

The second actuating device 522 includes a second elliptical element 526 in contact with the grid right-hand side 510 and a second spring 532. The second spring 532 is also attached to the support structure 540. The second elliptical element 526 has a major axis and a minor axis. The length of at least one of the major axis or the minor axis of the second elliptical element 526 is different from the length of the corresponding major axis or minor axis of the first elliptical element 524. The second elliptical element 526 is attached to a motor 544 that causes the second elliptical element 526 to rotate or spin. The first elliptical element 524 and the second elliptical element 526 may be attached to the same motor or different motors. The speed at which the first elliptical element 524 rotates and the speed at which the second elliptical element 526 rotates may be the same or different.

Two additional springs 534, 536 may also be in contact with the grid left-hand side 512 and another support structure 542. The other support structure 542 may be a portion of the breast platform housing or may be a separate structure that allows for retraction of the anti-scatter grid 500. The additional springs 534, 536 provide additional flexible constraints for the vibrational movement caused by rotating of the elliptical elements 524, 526. In other examples, greater or fewer additional springs may be used, or no additional springs need be utilized. While the actuating devices 520, 522 have been depicted as being in contact with the grid right-hand side 510, in other examples the configuration may be reversed such that the actuating devices 520, 522 are in contact with the grid left-hand side 512.

Because the major axis of the first elliptical element 524 has a different length than the element major axis of the second elliptical element 526, angular motion of the anti-scatter grid 500 can be achieved when the elliptical elements 524, 526 rotate. For example, when the first elliptical element 524 rotates, the grid gate-wall end 504 is moved a first distance based on the length of the major axis of the first elliptical element 524. Similarly, when the second elliptical element 526 rotates, the grid chest-wall surface 502 is moved a second distance based on the length of the major axis of the second elliptical element 526. To achieve the angular motion around the center of the radius of curvature of the grid chest-wall surface 502, the grid gate-wall end 504 may be moved a distance ($D_G$) equal to the quotient of the radius of curvature of the grid gate-wall end 504 ($R_G$) and the radius of curvature of the grid chest-wall surface 502 ($R_C$) multiplied by the distance ($D_C$) the grid chest-wall surface 502 moves. That relationship can be represented by the following equation:

$$D_G = \frac{R_G}{R_C} D_C$$

where $D_G$ is the distance the grid gate-wall end 504 moves, $D_C$ is the distance the grid chest-wall surface 502 moves, $R_G$ is the radius of curvature of the grid gate-wall end 504, and $R_C$ is the radius of curvature of the grid chest-wall surface 502. The sizes of the elliptical elements 524, 526 can thus be determine based on the above relationships. That is, the ratio of the length of the major axis of the first elliptical element 524 to the length of the major axis of the second elliptical element may be about $R_G/R_C$.

The following example may further illustrate the movement. Take for example an anti-scatter grid 500 where the radius of curvature of the grid chest-wall surface 502 is about 400 mm and the radius of curvature is about 641 mm. If the actuating device 522 is configured to move the grid chest-wall surface 502 about 10 mm along its radius of curvature, then the grid gate-wall end 504 should be moved about 16 mm. In an example where the actuating devices 520, 522 include elliptical elements 524, 526, the elliptical elements 524, 526 should be sized accordingly to accomplish such movement.

Figure 6:
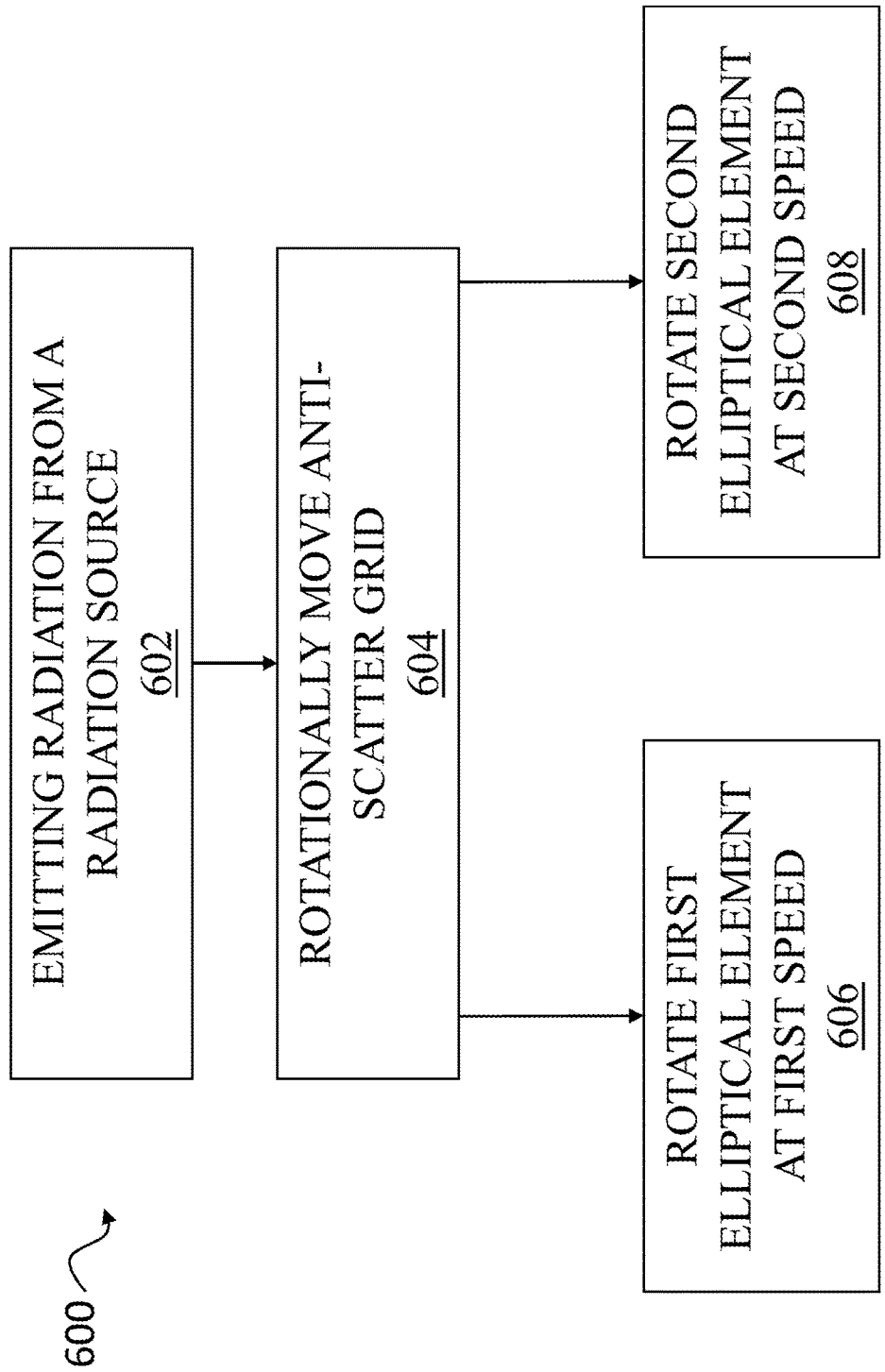
FIG. 6 depicts an example method for controlling an anti-scatter grid.

FIG. 6 depicts an example method 600 for controlling the anti-scatter grid. At operation 602, radiation is emitted from a radiation source. For example, radiation is emitted in the form of x-rays to pass through a breast and then be detected by an x-ray detector, such as the contoured radiation detector discussed herein. While the radiation is being emitted, an anti-scatter grid is rotationally moved at operation 604. The rotational movement of the anti-scatter grid may be angular movement around the center of curvature for a curved chest-wall surface of the x-ray detector or the anti-scatter grid. The rotational movement of the x-ray detector may be accomplished by rotating a first elliptical element at a first speed at operation 606 and rotating a second elliptical element at a second speed at operation 608. The first elliptical element and the second elliptical element are in contact with a lateral side of the anti-scatter grid. The first speed and the second speed may be the same speed.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A medical imaging system comprising:
    an x-ray radiation source configured to emit x-ray radiation;
    a contoured x-ray radiation detector configured to receive x-ray radiation emitted from the x-ray radiation source after the x-ray radiation has passed through at least a portion of a patient, wherein the contoured x-ray radiation detector includes:
        a gate-wall end;
        lateral sides, including a right-hand side and a left-hand side;
        a superior surface connected to the gate-wall end, the right-hand side, and the left-hand side; and
        a chest-wall surface having a radius of curvature, the chest-wall surface connected to the superior surface, the right-hand side, and the left-hand side, whereby the chest-wall surface is contoured to a chest wall of the patient; and
    an anti-scatter grid retractably positionable above the superior surface, wherein the anti-scatter grid includes:
        a grid gate-wall end;
        grid lateral sides, including a grid right-hand side and a grid left-hand side; and
        a grid chest-wall surface, wherein the grid chest-wall surface has a curvature substantially matching the radius of curvature of the chest-wall surface of the contoured x-ray radiation detector, and wherein the anti-scatter grid is configured to rotationally move around the radius of curvature when disposed above the superior surface.

2. The medical imaging system of claim 1, further comprising a plurality of actuating devices attached to the anti-scatter grid to control movement of the anti-scatter grid.

3. The medical imaging system of claim 2, wherein one or more of the plurality of actuating devices comprises a motor and an elliptical element, wherein the elliptical element is in contact with one of the grid lateral sides, wherein the motor is configured to rotate the elliptical element such that the anti-scatter grid moves in response to rotation of the elliptical element.

4. The medical imaging system of claim 2, wherein a first actuating device and a second actuating device, in the plurality of actuating devices, are in contact with one of the grid lateral sides.

5. The medical imaging system of claim 4, wherein:
    the first actuating device includes a first elliptical element, wherein the first elliptical element is in contact with one of the grid lateral sides; and
    the second actuating device includes a second elliptical element, wherein the second elliptical element is in contact with the one of the grid lateral sides.

6. The medical imaging system of claim 5, wherein the first elliptical element has a major axis and the second elliptical element has a major axis, wherein the major axis of the first elliptical element is greater than the major axis of the second elliptical element.

7. The medical imaging system of claim 5, wherein at least one of the first actuating device and the second actuating device includes a motor configured to rotate at least one of the first actuating device and the second actuating device.

8. The medical imaging system of claim 5, wherein at least one spring is attached to a grid lateral side opposite the grid lateral side in contact with the first actuating device and the second actuating device.

9. The medical imaging system of claim 5, further comprising a first spring, a second spring, a third spring, and a fourth spring, and wherein:
    the first elliptical element is in contact with the right-hand side and the first spring;
    the second elliptical element is in contact with the right-hand side and the second spring; and
    the left-hand side is in contact with the third spring and the fourth spring.

10. A method of medical imaging, the method comprising:
    emitting x-ray radiation from an x-ray radiation source; and
    while emitting x-ray radiation from the x-ray radiation source, rotationally moving an anti-scatter grid positioned between the x-ray radiation source and an x-ray radiation detector, wherein a chest-wall surface of the anti-scatter grid is curved and has a radius of curvature and wherein rotationally moving the anti-scatter grid comprises:
        rotating a first elliptical element at a first speed, wherein the first elliptical element is in contact with the anti-scatter grid; and
        rotating a second elliptical element at a second speed, wherein the second elliptical element is in contact with the anti-scatter grid.

11. The method of claim 10, wherein the first speed and the second speed are the same.

12. The method of claim 10, wherein the first elliptical element has a major axis and the second elliptical element has a major axis, and the major axis of the first elliptical element is greater than the major axis of the second elliptical element.

13. The method of claim 10, wherein rotationally moving the anti-scatter grid moves the anti-scatter grid around a center of curvature of the chest-wall surface of the anti-scatter grid.

14. A medical imaging system comprising:
   an x-ray radiation source configured to emit x-ray radiation;
   a contoured x-ray radiation detector configured to receive x-ray radiation emitted from the x-ray radiation source after the x-ray radiation has passed through at least a portion of a patient;
   an anti-scatter grid configured, wherein the anti-scatter grid includes:
      a grid gate-wall end;
      grid lateral sides, including a grid right-hand side and a grid left-hand side; and
      a contoured grid chest-wall surface having a radius of curvature; and
   a plurality of actuating devices attached to the anti-scatter grid to move the anti-scatter grid around a center of curvature of the grid chest-wall surface, wherein the plurality of actuating devices includes:
      a first actuating device including a first elliptical element, wherein the first elliptical element is in contact with one of the grid lateral sides; and
      a second actuating device including a second elliptical element, wherein the second elliptical element is in contact with the one of the grid lateral sides.

15. The medical imaging system of claim 14, wherein the first elliptical element has a major axis and the second elliptical element has a major axis, wherein the major axis of the first elliptical element is greater than the major axis of the second elliptical element.

16. The medical imaging system of claim 14, wherein at least one of the first actuating device and the second actuating device includes a motor configured to rotate at least one of the first actuating device and the second actuating device.

17. The medical imaging system of claim 16, wherein the motor is configured rotate the first elliptical element and the second elliptical element at the same speed.

18. The medical imaging system of claim 14, wherein at least one spring is attached to a grid lateral side opposite the grid lateral side in contact with the first actuating device and the second actuating device.

19. The medical imaging system of claim 14, further comprising a support structure coupled to the plurality of actuating devices for retracting the anti-scatter grid from a path of the emitted x-ray radiation.

\* \* \* \* \*